United States Patent [19]

Heimreid

[11] Patent Number: 4,978,342
[45] Date of Patent: Dec. 18, 1990

[54] EXUDATE-ABSORPTIVE, ADHESIVE-BACKED DERMAL PATCH FOR USE WHILE COLLECTING A BLOOD SAMPLE

[76] Inventor: Ken Heimreid, Jupiter Ring 41D, N-3942 Skjelsvik, Norway

[21] Appl. No.: 265,793
[22] PCT Filed: Feb. 17, 1988
[86] PCT No.: PCT/NO88/00013
§ 371 Date: Oct. 24, 1988
§ 102(e) Date: Oct. 24, 1988
[87] PCT Pub. No.: WO88/06427
PCT Pub. Date: Sep. 7, 1988

[30] Foreign Application Priority Data

Feb. 24, 1987 [NO] Norway ................................. 870737

[51] Int. Cl.⁵ .............................................. A61M 5/32
[52] U.S. Cl. ........................ 604/180; 128/DIG. 26; 128/760
[58] Field of Search ............... 604/180, 174, 179, 304, 604/305, 307, 264, 240; 128/155, 171, DIG. 26, 760, 762, 763, 767

[56] References Cited

U.S. PATENT DOCUMENTS

| | | | |
|---|---|---|---|
| 3,487,837 | 2/1967 | Petersen | 604/180 |
| 3,683,911 | 8/1972 | McCormick | 604/180 |
| 3,741,197 | 6/1973 | Sanz et al. | 428/770 |
| 3,782,377 | 1/1974 | Rychlik | 604/180 |
| 3,961,622 | 6/1976 | Edwards | 604/52 |
| 4,053,053 | 10/1977 | Tumangday | 128/155 |
| 4,078,568 | 3/1978 | Etes et al. | 128/155 |
| 4,080,970 | 3/1978 | Miller | 604/174 |
| 4,221,215 | 9/1980 | Mandelbaum | 128/155 |
| 4,329,999 | 5/1982 | Phillips | 128/760 |
| 4,519,793 | 5/1985 | Galindo | 128/DIG. 26 |
| 4,633,863 | 1/1987 | Filips et al. | 604/180 |
| 4,675,006 | 6/1987 | Hiushesky | 128/DIG. 26 |
| 4,767,411 | 8/1988 | Edmunds | 604/180 |

FOREIGN PATENT DOCUMENTS 2947427 11/1979 Fed. Rep. of Germany.

Primary Examiner—C. Fred Rosenbaum
Assistant Examiner—Kathleen A. Daley
Attorney, Agent, or Firm—Cushman, Darby & Cushman

[57] ABSTRACT

An adhesive-backed strip is stuck onto a patient's skin. The strip has an opening provided through it at the site where a blood sample is to be taken. On its outer side, the strip is provided with an upstanding annular collar surrounding the opening through the strip, thereby providing a sump bottomed by the surface of the subject's skin. The sump receives a plug of liquid-absorptive material. As the subject's skin is pierced by a cannula, inserted down through the sump, to take a blood sample, the initial exudate, including capillary blood and other tissue fluids, exudes into the sump where it is absorbed by the plug. Thereafter, venous blood is conventionally drawn into the cannula while the bandage remains in place.

1 Claim, 1 Drawing Sheet

EXUDATE-ABSORPTIVE, ADHESIVE-BACKED DERMAL PATCH FOR USE WHILE COLLECTING A BLOOD SAMPLE

BACKGROUND OF THE INVENTION

The present invention relates to a plaster, i.e. a prepared bandage in the form of an exudate-absorptive, adhesive-backed dermal patch for use while collecting a blood sample from an animate subject using a transcutaneous cannula, e.g. a hollow needle connected to a suction means.

In conventional blood sampling, immediately after penetration of the subject's dermis, e.g. of a fingertip, capillary blood and other dermal and tissue fluids are secreted. Since the object generally is to collect a sample of venous blood uncontaminated by the initial exudate, it is conventional to not collect the initial exudate, but to wipe it off, or to let it flow over the fingertip and drip off, e.g. onto the floor.

In this way, the bloody initial exudate is transferred to areas surrounding where the sample is taken.

In view of present requirements for improved hygiene, and to some extent in connection with public health concerns for the spread of hepatitis and AIDS, there is a need in the art for means for providing increased safety and hygiene in connection with taking blood samples. Further, there is a need in the art for means for facilitating the taking of venous blood samples little contaminated by initial exudate.

SUMMARY OF THE INVNETION

The present invention provides a prepared bandage designed to be stuck onto a subject's skin at a site where a blood sample is to be taken. The bandage includes a patch with an opening through it, the opening being surrounded by an outwardly projecting annular collar made of body fluid exudate-impermeable material. The collar thus provides a sump or well, in which is fitted a plug of body fluid absorptive material. In use, as the subject's skin, under the well, is punctured by a cannula, the initial exudate of capillary blood and other dermal and tissue fluids are absorbed into the plug of absorptive material, so that a relatively uncontaminated sample of venous blood can be collected through the cannula, without spreading and dripping of initial exudate fluid around the site of the sampling area.

The term cannula is used generically herein for whatever means is used to draw the subject's blood, since the particular means used is not part of the present invention.

BRIEF DESCRIPTION OF THE DRAWING

The invention may be better understood with reference to the attached drawing showing a preferred embodiment of the device of the present invention.

In the Drawing.

DETAILED DESCRIPTION

Figure 1:
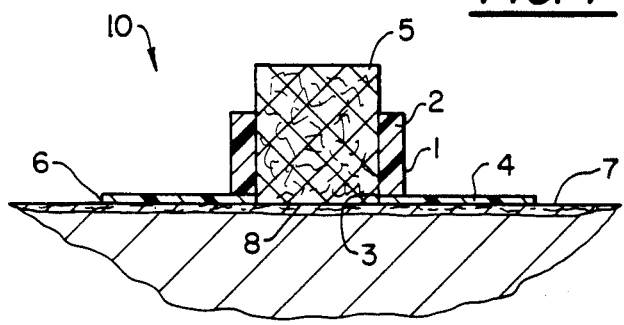
FIG. 1 is a longitudinal vertical cross-sectional view of an exudate-absorptive, adhesive-backed dermal patch for use while collecting a blood sample, this article being made in accordance with principles of the present invention.
Figure 2:
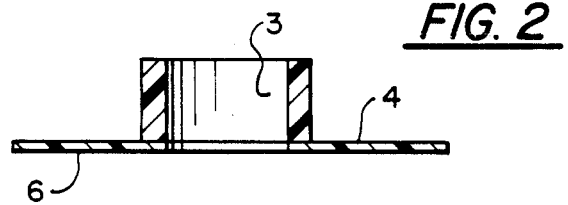
FIG. 2 is a longitudinal perspective view thereof similar to FIG. 1, but with the absorptive plug thereof removed to expose other details.
Figure 3:
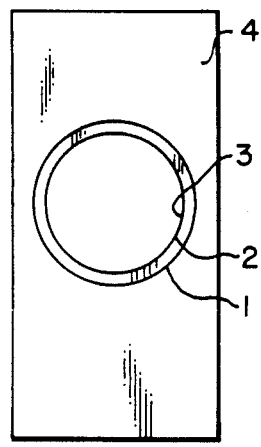
FIG. 3 is a top plan view of the partly disassembled structure shown in FIG. 2.

The plaster, i.e. prepared bandage 10 of the present invention comprises a strip 4 which is conventionally adhesive-backed, as at 6, so it can be stuck onto a subject's skin 7, surrounding the site 8 where a blood sample is to be taken.

At the site 8, the strip 4 has an opening 3 provided through it. An annular collar 1 is securely provided on the strip 4, so that the collar 1 extends outwards from the outer surface of the strip. The strip 4 and the collar 1 are made of a material, such as is conventionally used in manufacturing of strip-type prepared bandages, that is substantially impermeable to liquid exudate fluid expected from puncturing of the skin and subcutaneous tissue for taking a venous blood sample.

The radially inner surface 2 of the collar 1, together with the corresponding peripheral surface of the opening 3 provides a sump or well, the bottom of which is provided by the outer surfaces of the subject's skin 7.

The sump is fitted with a cylindrical plug 5 made of conventional absorptive material capable of absorbing liquid exudate expected from puncturing the skin and subcutaneous tissue for taking a venous blood sample.

The inner peripheral surface 2 of the sump may be impregnated with an anticoagulant, e.g. heparin. Furthermore, the exudate-absorbing member 5 may also be impregnated with matter such as will facilitate later examination of fluid and blood captured in the member 5.

In use, the bandage 10 may be stuck onto the skin of the subject, with a sample-taking needle (not shown) gripped between the outside of the member 5 and the inner surface 2 of the collar 1. As the needle is pushed inward, penetrating the skin and subcutaneous tissue, tissue fluid and capillary blood exudes through the puncture and into the sump, where it is absorbed by the member 5. Venous blood is then conventionally drawn into the needle and collected for sampling.

It should now be apparent that the exudate-absorptive, adhesive-backed dermal patch for use while collecting a blood sample as described hereinabove, possesses each of the attributes set forth in the specification under the heading "Summary of the Invention" hereinbefore. Because it can be modified to some extent without departing from the principles thereof as they have been outlined and explained in this specification, the present invention should be understood as encompassing all such modifications as are within the spirit and scope of the following claims.

I claim:

1. A prepared bandage for use while collecting a blood sample from an animate subject using a transcutaneous cannula,
    said bandage comprising:
        an adhesive-backed strip arranged to be stuck onto the skin of the subject, said strip having means defining an opening therethrough for surrounding a site where a blood sample is to be taken;
        an annular, upstanding collar secured on said strip surrounding said opening so that an inner peripheral surface of said strip surrounding said opening and an inner peripheral surface of said collar, provide a sump, bottomed, in use, by the subject's skin;
        a plug made of absorptive material capable of absorbing liquid exudate expected from puncturing the skin and subcutaneous tissue for taking venous blood from the subject, said plug being received in said sump and engaged by said inner peripheral surface of said collar so as to be retained in said sump.

* * * * *